(12) United States Patent
Larrain et al.

(10) Patent No.: US 7,192,419 B2
(45) Date of Patent: Mar. 20, 2007

(54) MEDIUM CRACKING PRESSURE VALVE ARRANGEMENT

(75) Inventors: Ignacio Larrain, Preverenges (CH); Michael Jedwab, Lausanne (CH)

(73) Assignee: Nestec S.A., Vevey (CH)

(*) Notice: Subject to any disclaimer, the term of this patent is extended or adjusted under 35 U.S.C. 154(b) by 0 days.

(21) Appl. No.: 09/681,896

(22) Filed: Jun. 21, 2001

(65) Prior Publication Data
US 2002/0002350 A1    Jan. 3, 2002

(30) Foreign Application Priority Data
Jun. 29, 2000    (EP)    ................ 00113777

(51) Int. Cl.
*A61M 5/00*    (2006.01)
(52) U.S. Cl. .................................. 604/247
(58) Field of Classification Search .......... 604/247, 604/256, 30, 31, 34, 250, 246; 251/12, 84, 251/318, 336
See application file for complete search history.

(56) References Cited

U.S. PATENT DOCUMENTS

| | | | |
|---|---|---|---|
| 4,244,378 A * | 1/1981 | Brignola ................. 604/247 |
| 4,845,487 A * | 7/1989 | Frantz et al. ............ 340/679 |
| 4,946,448 A * | 8/1990 | Richmond ................ 604/247 |
| 5,009,654 A * | 4/1991 | Minshall et al. .......... 604/410 |
| 5,025,829 A * | 6/1991 | Edwards et al. .......... 604/247 |
| 5,244,463 A * | 9/1993 | Cordner et al. .......... 604/131 |
| 5,535,785 A * | 7/1996 | Werge et al. ............ 604/249 |
| 5,617,897 A | 4/1997 | Myers |
| 5,660,205 A | 8/1997 | Epstein |
| 5,738,662 A * | 4/1998 | Shannon et al. ......... 604/247 |
| 6,059,747 A | 5/2000 | Bruggeman et al. |
| 6,409,707 B1 * | 6/2002 | Guala ..................... 604/247 |

FOREIGN PATENT DOCUMENTS

EP    0 934 757    8/1999

* cited by examiner

Primary Examiner—Nicholas D. Lucchesi
Assistant Examiner—Matthew F. DeSanto
(74) Attorney, Agent, or Firm—Bell, Boyd & Lloyd LLP

(57) ABSTRACT

A valve arrangement for providing clinical nutrition is provided. The valve arrangement is suitable for use with a rotary peristaltic pump and is capable of allowing flow of fluid in a first direction and capable of preventing flow of fluid in a second direction, wherein the valve arrangement comprises a valve having a cracking pressure of about 0.10 to about 0.20 bar. Also described are a method of production of the valve arrangement, use of the valve arrangement in providing nutrition to a patient and a method of treatment of a patient that comprises administering an effective amount of a composition via the valve arrangement.

11 Claims, 1 Drawing Sheet

MEDIUM CRACKING PRESSURE VALVE ARRANGEMENT

BACKGROUND OF THE INVENTION

The present invention relates to a valve arrangement for providing clinical nutrition, a flow set comprising the valve arrangement, a method for producing the valve arrangement, use of the valve arrangement in providing nutrition, and methods of treating patients by administering an effective amount of a liquid composition through the valve arrangement.

Hospital patients are routinely provided fluids for maintaining a good state of hydration. Furthermore, fluid can act as a carrier for nutrients in order to provide a patient with adequate nutrition, for example, following surgery.

Systems for the administration of fluids to a patient are widely known. The manner of propelling the fluid to a patient may be by gravitation; by means of pressure applied on a deformable container; or by means of a pump. In pump-operated administration systems, the pump must be capable of administering the fluid in a controlled, generally continuous manner.

Pumps are employed to meet the need for a high degree of accuracy in the administration of fluids, to protect the patient and to maximize the effectiveness of medication.

An example of a pump that is presently used for pumping fluid through a tube to a patient is a rotary peristaltic pump. This type of pump suffers from the disadvantage that if the flow set, the tubing through which the fluid is pumped, is not connected properly or is disconnected from the pump, a free-flow condition can occur. Furthermore, in general, this type of pump does not have antifree-flow protection. Uninhibited free flow of fluid to a patient can be dangerous for the patient, e.g., it can lead to drowning.

Another example of a pump presently used to administer fluid to a patient is a linear peristaltic pump. This type of pump suffers from the problem that if the flow set is not connected properly, it is subject to a (pumped) back flow of liquid in a direction opposite to the intended direction of flow to a patient. It is clear that if a free flow or back flow of fluid proceeds unchecked, it can be dangerous for a patient.

To cope with the problem of free flow, a piece of apparatus known as an occluder has been used. The occluder operates by folding a length of resilient tubing, thereby pinching the tubing and causing its internal diameter to be reduced, thereby inhibiting flow therethrough. This arrangement works, but it has been found that it suffers from the problems that if an elastic part of the occluder (for keeping a resilient tube folded) is over stretched, it can be broken easily. Therefore, if an operator disconnects the pump, but fails to close the tubing, for example with a roller clamp, a free flow condition may occur.

Therefore, a need exists for an apparatus which permits a good flow of fluid to a patient, but which addresses the problems presented by uninhibited free flow and flow back.

SUMMARY OF THE INVENTION

It is believed that the present invention addresses the problems set out above. In this regard, the present invention provides an improved valve arrangement and devices utilizing same. Additionally, improved methods of providing fluid are provided.

Within the context of this specification the word "comprises" is taken to mean "includes, among other things". It is not intended to be construed as "consists of only".

"Flow back" is taken to mean the flow of fluid in a direction away from a patient.

"Free flow" is taken to mean the flow of fluid which occurs passively by gravity, generally without the intervention of a mechanical device such as a pump. It is characterized by a state of inactive pump operation. Free flow can be very harmful to patients as it can lead to aspiration of fluid into lungs.

"Cracking Pressure" is taken to mean the threshold pressure at which flow is allowed to occur. If the pressure of fluid across a valve is below this threshold, flow is not permitted.

Remarkably, it has now been found that a valve having a critical narrow range of cracking pressure can prevent the flow of fluid from a patient and restrict the free flow in the opposite direction. This can provide a high level of safety for the patient. Surprisingly, it has been found that this can be achieved by reducing free flow to a level which is not dangerous. In contrast, previous attempts were made to eliminate free flow entirely. It has now been found that this is not necessary.

Consequently, in an embodiment, the present invention provides a valve arrangement which is suitable for use with a rotary peristaltic pump and which is capable of allowing the flow of fluid in a first direction and capable of preventing the flow of fluid in a second direction. The valve arrangement comprises a valve having a cracking pressure of approximately 0.10 to about 0.20 bar.

In another embodiment, the invention provides a flow set for the administration of at least one fluid to a patient which comprises: a valve arrangement having a cracking pressure of approximately 0.10 to about 0.20 bar; an inlet tube for connecting a container to an inlet port of the valve; and an outlet tube for connecting to an outlet of the valve for the delivery of a fluid to a patient.

In a further embodiment, the invention provides a method of production of the valve arrangement which comprises producing a chamber, making ports including an inlet port and an outlet port, fixing a one way valve between the inlet port and the outlet port for allowing fluid to flow in only one direction, wherein the cracking pressure of the valve is about 0.10 to 0.20 bar.

In an embodiment, the invention provides a method for providing nutrition to a patient including the use of a valve having a cracking pressure of approximately 0.10 to about 0.20 bar. The nutrition is provided though the use of a liquid that is pumped into the patient. The liquid can, in an embodiment, provide the complete nutritional needs to the patient.

In an embodiment, the invention provides methods of treating patients comprising administering an effective amount of a fluid via a valve arrangement having a cracking pressure of approximately 0.10 to about 0.20 bar.

The valve arrangements of the invention provides numerous advantages. An advantage of the present invention is that it permits a simple and safe method of administering a fluid from a container to a patient. If the pressure of fluid across the valve assembly exceeds a predetermined cracking pressure, flow is permitted, but unless the cracking pressure is exceeded, for example by a pump, flow of fluid is not permitted through the valve assembly. During normal use, the height of the container may be such so as to generate a static pressure that slightly exceeds the cracking pressure of the valve. If, in addition, the set has been disconnected from the pump, flow of fluid through the valve assembly is restricted—i.e., free flow is inhibited to a degree so that any leakage by the valve presents no risk to the patient. In contrast, known valve arrangements have suffered from the problem that they have allowed a high flow rate of free flow to occur from a container to a patient if the set is misloaded or unloaded from the associated pump.

Another advantage provided by the present invention is that the volume of programmed flow by the pump is not affected by the valve arrangement. This is a result of a reduction of impedance of the valve arrangement.

Another advantage of the present invention is that no disconnection of tubing, no manual adjustment of valves or use of other equipment for blocking flow is required. Therefore, the flow of fluid from the valve arrangement can be accurately controlled. Furthermore, in view of the fact that no disconnection of tubing is required during use, the risk of contamination is reduced.

In addition, no special software or mechanical modification of the pump is required.

Yet another advantage of the present invention is that it provides an arrangement that is easy and inexpensive to manufacture. A simple manufacturing method can be carried out comprising a simple housing and piston or membrane and this increased simplicity adds to the speed at which production can be achieved.

Furthermore, if a valve arrangement according to the invention is used, fewer pieces of commercially available apparatus (such as pinch-clip occluders or roller clamps) are required.

Moreover, although a valve arrangement in accordance with the present invention is suitable for use with a rotary peristaltic pump, it is not limited to use with only this type of pump or any particular type of flow set. In contrast, known arrangements have been limited in this way.

Additional features and advantages of the present invention are described in, and will be apparent from, the description of the presently preferred embodiments which are set out below with reference to the drawings in which:

DETAILED DESCRIPTION OF THE INVENTION

Figure 1:
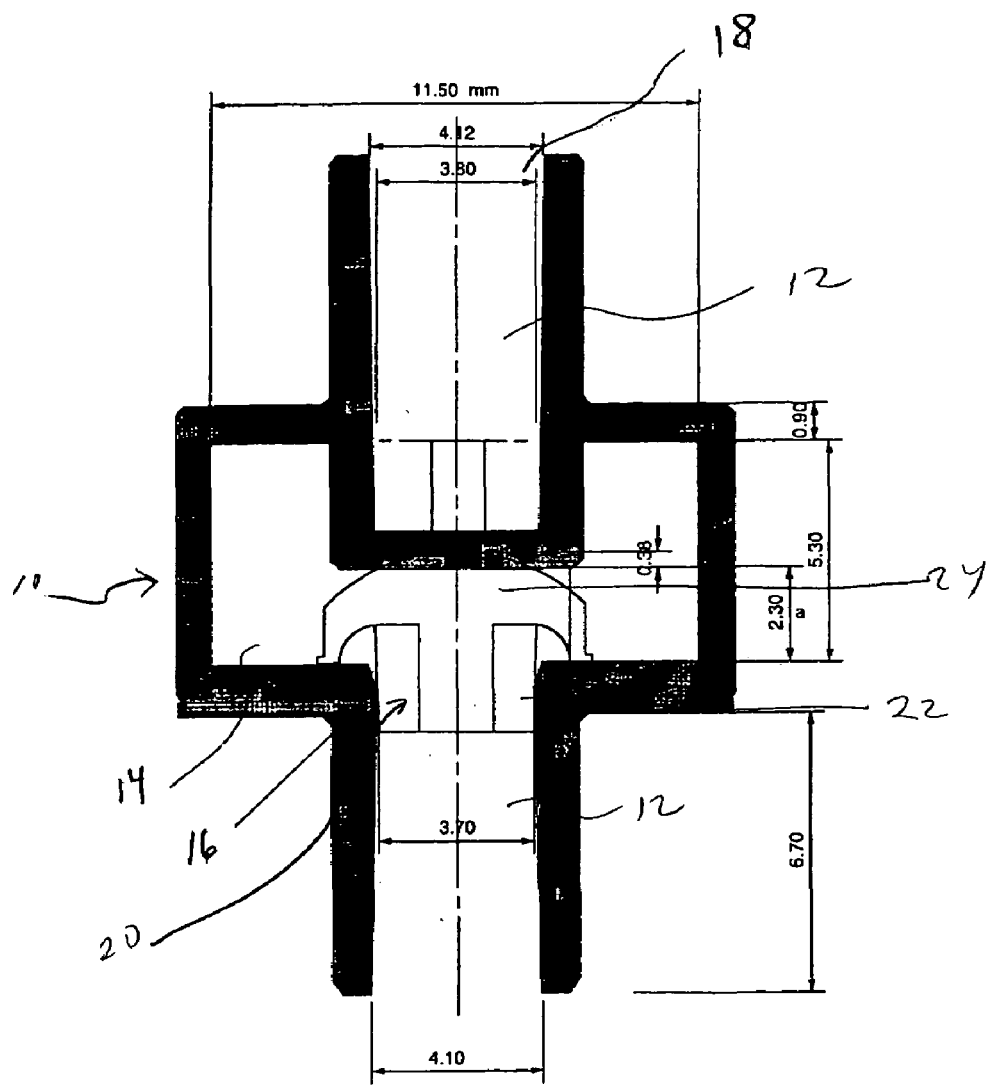
FIG. 1 illustrates an embodiment of the valve arrangement of the present invention.

The present invention provides improved valve arrangements, methods of manufacturing same, and methods of treatments using same. The valve arrangement has a cracking pressure of approximately 0.10 to about 0.20 bar. Preferably, in an embodiment of the valve arrangement according to the present invention the valve has a cracking pressure of approximately 0.12 bar to about 0.18 bar. In a most preferable embodiment, the cracking pressure is about 0.15 bar.

Remarkably, it has now been found that the specific cracking pressure of the valve of the invention provides a number of advantages. It is not merely a result of optimization of known apparatus. Indeed, it is believed that the specific cracking pressure could not have been arrived at logically without first making an inventive step by realizing that a cracking pressure could be important specifically in the administration of a fluid to a patient.

It has been found that these cracking pressures provide the advantage that, if a pump is disconnected from the valve arrangement, fluid is not able to pass through the outlet valve to a patient (or only a small amount of fluid). Therefore, uncontrolled flow to a patient is prevented. It has also been found that these cracking pressures provide the advantage that they do not alter a pump's operation, as they are sufficiently low to avoid any slippage in a peristaltic mechanism.

Preferably, in an embodiment of the present invention a valve is provided which comprises a flexible membrane which is deformable under pressure in a desired flow direction. The flexible membrane has perforations through it which open at a selected extent of deformation of the flexible membrane to permit flow. The valve assembly may be provided with a support associated with the flexible membrane for preventing the flexible membrane from deforming sufficiently in a direction opposite to the flow direction for preventing back flow. In accordance with a preferred embodiment of the invention, the membrane of the valve deforms at a predetermined cracking pressure.

Preferably, an embodiment of a valve arrangement according to the present invention is obtained by modification of known apparatus. Suitable starting materials are for example: a housing manufactured of metal or plastics material, preferably rigid plastics material including ABS, polycarbonate, PVC, acrylic or MABS; and a valve membrane manufactured of a resilient material including polyurethane, silicone or rubber.

Referring now to FIG. 1, a valve arrangement 10 according to an embodiment of the invention is illustrated. The valve comprises a channel 12 and a chamber 14. Fluid passes through the channel 12 via the chamber 14. The chamber has an annular inlet 16 and an annular outlet 18. A resilient piston 20 having a stem 22 and a mushroom shaped head 24 is located within the chamber. The piston 20 is constructed of flexible material, typically a sterilizable material such as silicon, rubber or any other suitable material.

In a rest state, the mushroom shaped head 24 blocks the channel 12 at the inlet 16 of the chamber 14. In an embodiment, when the pressure of fluid at the inlet 16 exceeds the pressure in the chamber 14 by a cracking pressure of at least about 0.15 bar (15 kPa), the head 24 deforms and/or the piston 20 deforms and/or shifts axially in the channel. This unblocks the channel at the inlet 16 of the chamber 14 and allows flow of fluid. Movement of the piston 20 relative to the channel is restricted by a stopper which engages the apex of the mushroom shaped head. In contrast, in an embodiment, where the pressure differential is lower than 0.15 bar or negative, the head of the piston blocks flow of fluid. This prevents undesired free flow of the fluid from the container.

The cracking pressure can be predetermined by setting the degree of compression of the mushroom shaped head. In the alternative, the cracking pressure can be set by setting the tension in the stem which exists during the rest state.

A pump of the pump unit is coupled to the valve arrangement via a tubing. The pump is preferably a peristaltic pump, but any pump which is able to pump fluid at controlled flow rates and which is suitable for clinical applications may be used.

The pump unit may include a control unit. The control unit typically comprises a control panel which has a display and a key pad. The key pad may be used for manual control of the pump, data entry, and the like. The control unit may include a microprocessor for controlling and activating the pump. A memory may be associated with, or be incorporated in, the microprocessor. If desired, the control unit may include an audio, visual or dual alarm signaling means.

A flow set comprising the valve arrangement is typically mounted on a stand with a container for fluid being held by an arm at the top of the stand. Drip chambers may be provided adjacent the outlet of the valve arrangement or between the container and the inlet of the valve arrangement.

In use, a pump pumps fluid from a container to a patient. Prior to pumping by the pump, the piston is in a rest state. When fluid is pumped through the inlet tube and a selected threshold pressure differential is reached, the piston is stretched and/or moved axially in the channel and/or the head of the piston deforms. This unblocks the inlet of the chamber and flow of fluid through the valve arrangement from the inlet tube into the outlet tube is permitted.

An alternative valve arrangement according to an embodiment of the invention comprises a housing having a channel and a chamber. A flexible membrane is held across the channel. The flexible membrane is made of a resilient flexible material, typically a sterilizable material such as silicon, rubber or any other suitable material. The membrane has a plurality of slits (for example two) which, in the rest state, are closed and do not permit flow of fluid. Typically, the membrane is designed so that its slits will open only when the pressure differential over the membrane exceeds about 0.15 bar (15 kPa). This prevents undesired free flow of the fluid from the container.

In use, a pump pumps fluid from a container to a patient. Prior to pumping by the pump, the flexible membrane is in a rest state. When fluid is pumped through the inlet tube, the flexible membrane is stretched. Once a selected threshold pressure differential is reached and the flexible membrane is sufficiently stretched, it deforms and slits in the membrane widen and open to allow flow of fluid from the inlet tube into the outlet tube.

Methods of treatment using the system of the present invention are provided. The methods include the steps of administering a fluid from a container to a patient using a pump to propel the fluid and a valve arrangement according to an embodiment of the invention. Although any fluid can be pumped, in an embodiment, the fluid is a nutritional solution. The nutritional solution can provide complete nutrition to the patient.

The system provides a safe and rapid means of administering a fluid to a patient which is extremely simple to operate.

It will be appreciated that numerous modifications may be made to the preferred embodiments without departing from the spirit and scope of the invention as set out in the claims.

The invention claimed is:

1. A valve arrangement suitable for use with a rotary peristaltic pump and which is capable of allowing a flow of fluid in a first direction and capable of preventing the flow of fluid in a second direction, wherein the valve arrangement comprises
    a valve having a cracking pressure of approximately 0.10 to about 0.20 bar wherein the valve consists essentially of
    a piston member, said piston member including a single stem and a mushroom-shaped head having an apex, wherein said apex engages a stopper adapted to restrict a movement of the piston member, and wherein said mushroom-shaped head is deformable under pressure in a desired flow direction.

2. The valve arrangement of claim 1 wherein the cracking pressure is about 0.15 bar.

3. A device for the administration of at least one fluid to a patient comprising:
    a valve arrangement including a valve consisting essentially of a piston member, said piston member including a single stem and a mushroom shaped head having an apex, wherein said apex engages a stopper adapted to restrict a movement of the piston member, and wherein said mushroom-shaped head is deformable under pressure in a desired flow direction and having a cracking pressure of approximately 0.10 to about 0.20 bar; and wherein said valve arrangement further comprises
    an inlet tube for providing, at least in part, a fluid flow path between a container and an inlet port of the valve arrangement, and
    an outlet tube for providing, at least in part, a fluid flow path between an outlet of the valve arrangement and a patient.

4. The device of claim 3 wherein the valve arrangement is coupled to a rotary peristaltic pump.

5. A method of providing a fluid to a patient comprising the steps of administering an effective amount of a fluid via a valve arrangement including a valve having a cracking pressure of approximately 0.10 to about 0.20 bar wherein the valve consists essentially of a piston member, said piston member including a single stem and a mushroom-shaped head having an apex, wherein said apex engages a stopper adapted to restrict a movement of the piston member, and wherein said mushroom-shaped head is deformable under pressure in a desired flow direction.

6. The method of claim 5 wherein the fluid provides nutrition to the patient.

7. The method of claim 5 wherein the fluid provides complete nutrition to the patient.

8. A method of treating a patient comprising the steps of administering a fluid from a container to a patient using a pump to propel the fluid via a valve arrangement including a valve having a cracking pressure of approximately 0.10 to about 0.20 bar wherein the valve consists essentially of a piston member, said piston member including a single stem and a mushroom-shaped head having an apex, wherein said apex engages a stopper adapted to restrict a movement of the piston member, and wherein said mushroom-shaped head is deformable under pressure in a desired flow direction.

9. The method of claim 8 wherein the valve arrangement is coupled to a peristaltic pump.

10. A device for controlling the flow of a fluid from a container to a patient including a valve arrangement including a valve that is so constructed and arranged to prevent the flow of fluid to a patient at certain conditions, allow the flow of fluid to a patient at a cracking pressure, and allow a certain level of a free flow of fluid to the patient wherein the valve consists essentially of a piston member said piston member including a single stem and a mushroom-shaped head having an apex, wherein said apex engages a stopper adapted to restrict a movement of the piston member, and wherein said mushroom-shaped head is deformable under pressure in a desired flow direction.

11. The device of claim 10 wherein the cracking pressure is approximately 0.1 to about 0.2 bar.

* * * * *